(12) United States Patent
Asako et al.

(10) Patent No.: US 7,754,454 B2
(45) Date of Patent: *Jul. 13, 2010

(54) PROCESS FOR PRODUCING SULFUR-CONTAINING HYDROXYCARBOXYLIC ACID

(75) Inventors: Hiroyuki Asako, Toyonaka (JP); Koji Hagiya, Ibaraki (JP)

(73) Assignee: Sumitomo Chemical Co., Ltd., Tokyo (JP)

( * ) Notice: Subject to any disclaimer, the term of this patent is extended or adjusted under 35 U.S.C. 154(b) by 417 days.

This patent is subject to a terminal disclaimer.

(21) Appl. No.: 11/575,446

(22) PCT Filed: Sep. 2, 2005

(86) PCT No.: PCT/JP2005/016569

§ 371 (c)(1),
(2), (4) Date: Sep. 27, 2007

(87) PCT Pub. No.: WO2006/030698

PCT Pub. Date: Mar. 23, 2006

(65) Prior Publication Data

US 2008/0124773 A1    May 29, 2008

(30) Foreign Application Priority Data

Sep. 17, 2004    (JP) .............................. 2004-271235

(51) Int. Cl.
*C12P 11/00*    (2006.01)

(52) U.S. Cl. .................... 435/130; 435/136; 435/252.1; 435/252.5; 435/253.3

(58) Field of Classification Search ................. 435/130, 435/136, 252.1, 252.5, 253.1
See application file for complete search history.

(56) References Cited

U.S. PATENT DOCUMENTS

| | | |
|---|---|---|
| 7,459,588 B2 | 12/2008 | Hagiya |
| 7,485,757 B2 | 2/2009 | Hagiya |
| 2009/0053781 A1 | 2/2009 | Hagiya et al. |

FOREIGN PATENT DOCUMENTS

| | | |
|---|---|---|
| EP | 0354529 A3 | 2/1990 |
| EP | 1260500 A1 | 11/2002 |
| JP | 52108088 A | 9/1977 |
| JP | 56-21593 A | 2/1981 |
| JP | 2001054380 A | 2/2001 |
| WO | 02/33110 A3 | 4/2002 |

OTHER PUBLICATIONS

Database WPI Week 197742 Thomson Scientific, London, GB; AN 1977-75202Y, XP002486514.
Database WPI Week 200137 Thomson Scientific, London, GB; AN 2001-347641, XP002485712.

*Primary Examiner*—Sandra Saucier
*Assistant Examiner*—Susan Hanley
(74) *Attorney, Agent, or Firm*—Sughrue Mion, PLLC

(57) ABSTRACT

A process for producing a sulfur-containing α-hydroxycarboxylic acid compound, which comprises a step for reacting a sulfur-containing dihydroxy compound with a cell or a material from treated cell of a microorganism that has an ability to convert the sulfur-containing dihydroxy compound to a corresponding α-hydroxycarboxylic acid compound.

2 Claims, No Drawings

PROCESS FOR PRODUCING SULFUR-CONTAINING HYDROXYCARBOXYLIC ACID

This application is a national stage of International Application No. PCT/JP2005/016569, filed Sep. 2, 2005, which claims the benefit of priority to JP 2004-271235, filed Sep. 17, 2004, and all of the disclosures of which are nearby incorporated by reference in their entirety.

TECHNICAL FIELD

The present invention relates to a process for producing a sulfur-containing hydroxycarboxylic acid.

BACKGROUND ART

Conventionally, as processes for producing a sulfur-containing hydroxycarboxylic acid, a process for hydrolyzing cyanhydrin using sulfuric acid as a catalyst, a process for hydrolyzing a hydroxynitrile compound through action of a microorganism to convert into a corresponding hydroxycarboxylic acid (e.g., Japanese Patent Laid-Open for Opposition No. 58-15120, Japanese Patent Application Laid-Open (JP-A) No. 2-84198, JP-A-4-40898), and the like are known.

However, in the process using sulfuric acid as a catalyst, the reaction between a hydroxynitrile compound and sulfuric acid produces the objective compound, a hydroxycarboxylic acid, and an equimolar amount of ammonium sulfate as a byproduct. Accordingly, since the process requires a step for collecting the byproduct, there is a problem that the steps are made complicate and production costs increase.

Furthermore, the process for producing a hydroxycarboxylic acid compound from a corresponding hydroxynitrile compound using a microorganism has problems that cyanogen and the like generated by degradation of the hydroxynitrile compound inhibit the enzymatic activity of the microorganism; and that the production costs increase since the process requires desalting treatment of the produced ammonium salt, and the like.

The present inventors have investigated to find a process for producing a sulfur-containing hydroxycarboxylic acid that does not use a hydroxynitrile compound as a raw material, and found that the primary hydroxyl group of a sulfur-containing dihydroxy compound can be preferentially oxidized by using a cell or a material from treated cell of a microorganism that can convert a sulfur-containing dihydroxy compound to a corresponding α-hydroxycarboxylic acid compound, resulting in the completion of the present invention.

DISCLOSURE OF THE INVENTION

The objective of the present invention is providing a process for production that enables efficient production of a sulfur-containing hydroxycarboxylic acid compound.

Namely, the present invention provides the following items [1] to [4]:

[1] A process for producing (hereinafter sometimes referred to as the process of the present invention) a sulfur-containing α-hydroxycarboxylic acid compound represented by the general formula (2):

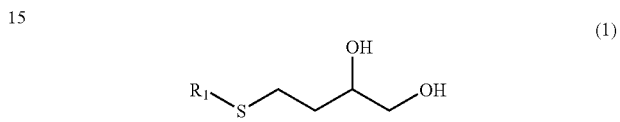

wherein
R$_1$ represents a hydrogen atom, an alkyl group having 1 to 8 carbon atoms or an aryl group having 6 to 20 carbon atoms,
which comprises a step for reacting a sulfur-containing dihydroxy compound represented by the general formula (1):

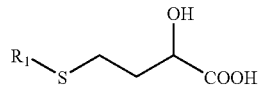

wherein R$_1$ is as defined above,
with a cell or a material from treated cell of a microorganism that has an ability to convert the sulfur-containing dihydroxy compound to a corresponding α-hydroxycarboxylic acid compound (hereinafter sometimes referred to as the present microorganism);

[2] The process according to the item [1], wherein the microorganism is at least one kind of microorganism selected from the group consisting of genus *Alcaligenes*, genus *Bacillus*, genus *Pseudomonas*, genus *Rhodobacter* and genus *Rhodococcus*;

[3] The process according to the item [1] or [2], wherein R$_1$ in the sulfur-containing dihydroxy compound represented by the general formula (1) is an alkyl group having 1 to 8 carbon atoms; and

[4] Use of a cell or a material from treated cell of a microorganism as a catalyst for preferentially oxidizing the primary hydroxyl group of a sulfur-containing dihydroxy compound represented by the general formula (1);

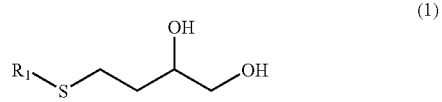

wherein
R$_1$ represents a hydrogen atom, an alkyl group having 1 to 8 carbon atoms or an aryl group having 6 to 20 carbon atoms.

BEST MODE FOR CARRYING OUT THE INVENTION

The process for producing a sulfur-containing α-hydroxycarboxylic acid compound according to the present invention (hereinafter sometimes referred to as the process of the present invention) comprises a step for reacting a sulfur-containing dihydroxy compound represented by the above-mentioned general formula (1) with a cell or a material from treated cell of a microorganism that has an ability to convert the sulfur-containing dihydroxy compound to a corresponding α-hydroxycarboxylic acid compound (hereinafter sometimes referred to as the present microorganism).

In the sulfur-containing dihydroxy compound represented by the general formula (1) and the sulfur-containing hydroxycarboxylic acid compound represented by the general formula (2), examples of the alkyl group having 1 to 8 carbon atoms represented by $R_1$ may include a methyl group, an ethyl group, a propyl group, an isopropyl group, a butyl group, an isobutyl group, a t-butyl group, a pentyl group, a hexyl group, a heptyl group, an octyl group, and the like.

Examples of the aryl group having 6 to 20 carbon atoms represented by $R_1$ may include a phenyl group, a tolyl group, a naphthyl group, and the like.

$R_1$ for the sulfur-containing dihydroxy compound represented by the general formula (1) is preferably an alkyl group having 1 to 8 carbon atoms.

The sulfur-containing hydroxycarboxylic acid compound represented by the general formula (2) obtained from the corresponding sulfur-containing dihydroxy compound represented by the general formula (1), which is produced by the process of the present invention and collected from the reaction solution, may be in the form of a salt.

The cell or material from treated cell of the microorganism, which is used as a catalyst for the present invention, may be a cell or a material from treated cell of a microorganism that has an ability to convert a sulfur-containing hydroxycarboxylic acid compound to a corresponding α-hydroxycarboxylic acid.

Examples of such a cell or material from treated cell of the microorganism include a cell or material from treated cell of:

microorganisms belonging to genus *Alcaligenes* such as *Alcaligenes faecalis, Alcaligenes denitrificans, Alcaligenes eutrophus, Alcaligenes* sp., *Alcaligenes xylosoxydans*, and the like;

microorganisms belonging to genus *Bacillus* such as *Bacillus alvei, Bacillus badius, Bacillus brevis, Bacillus cereus, Bacillus circulans, Bacillus coagulans, Bacillus firmus, Bacillus lentus, Bacillus licheniformis, Bacillus macerans, Bacillus megaterium, Bacillus moritai, Bacillus mycoides, Bacillus polymyxa, Bacillus pumilus, Bacillus sphaericus, Bacillus subtilis, Bacillus thuringenesis, Bacillus validus*, and the like;

microorganisms belonging to genus *Pseudomonas* such as *Pseudomonas auricularis, Pseudomonas azotoformans, Pseudomonas caryophylli, Pseudomonas chlororaphis, Pseudomonas denitrificans, Pseudomonas diminuta, Pseudomonas fluorescens, Pseudomonas fragi, Pseudomonas fulva, Pseudomonas mendocina, Pseudomonas mutabilis, Pseudomonas nitroreducens, Pseudomonas oleovorans, Pseudomonas ovalis, Pseudomonas oxalaticus, Pseudomonas plantarii, Pseudomonas pseudoalcaligenes, Pseudomonas putida, Pseudomonas putrefaciens, Pseudomonas riboflavina, Pseudomonas* sp., *Pseudomonas straminea, Pseudomonas synxantha, Pseudomonas syringae, Pseudomonas tabaci, Pseudomonas taetrolens, Pseudomonas vesicularis*, and the like;

microorganisms belonging to genus *Rhodobacter* such as *Rhodobacter sphaeroides*; and microorganisms belonging to genus *Rhodococcus* such as *Rhodococcus erythropolis, Rhodococcus groberulus, Rhodococcus rhodochrous, Rhodococcus* sp., and the like.

Specific examples may include a cell or material from treated cell of:

*Alcaligenes faecalis* IFO13111t, *Alcaligenes denitrificans* JCM5490, *Alcaligenes eutrophus* ATCC43123, *Alcaligenes* sp. IFO14130, *Alcaligenes xylosoxydans* IFO15125t, *Bacillus alvei* IFO3343t, *Bacillus badius* ATCC14574t, *Bacillus brevis* IFO12334, *Bacillus cereus* JCM2503t, *Bacillus circulans* ATCC13403, *Bacillus coagulans* JCM2257t, *Bacillus firmus* JCM2512t, *Bacillus lentus* JCM2511t, *Bacillus licheniformis* IFO12195, *Bacillus macerans* JCM2500t, *Bacillus megaterium* IFO12108, *Bacillus moritai* ATCC21282, *Bacillus mycoides* IFO3039, *Bacillus polymyxa* IFO3020, *Bacillus pumilus* IFO12092t, *Bacillus sphaericus* IFO3341, *Bacillus subtilis* JCM1465t, *Bacillus thuringenesis* ATCC13366, *Bacillus validus* IFO13635, *Pseudomonas auricularis* IFO13334t, *Pseudomonas azotoformans* JCM2777t, *Pseudomonas caryophylli* IFO13591, *Pseudomonas chlororaphis* IFO3121t, *Pseudomonas denitrificans* IAM1923, *Pseudomonas diminuta* JCM2788t, *Pseudomonas fluorescens* IFO14160t, *Pseudomonas fragi* IFO3458t, *Pseudomonas fulva* JCM2780t, *Pseudomonas mendocina* IFO14162, *Pseudomonas mutabilis* ATCC31014, *Pseudomonas nitroreducens* JCM2782t, *Pseudomonas oleovorans* IFO135835, *Pseudomonas ovalis* IFO12688, *Pseudomonas oxalaticus* IFO13593t, *Pseudomonas plantarii* JCM5492t, *Pseudomonas pseudoalcaligenes* JCM5968t. *Pseudomonas putida* IFO3738, *Pseudomonas putida* IAM1002, *Pseudomonas putida* IAM1090, *Pseudomonas putida* IAM1236, *Pseudomonas putida* ATCC39213, *Pseudomonas putrefaciens* IFO3910, *Pseudomonas riboflavin* IFO13584t, *Pseudomonas* sp. ATCC53617, *Pseudomonas straminea* JCM2783t, *Pseudomonas synxantha* IFO3913t, *Pseudomonas syringae* IFO14055, *Pseudomonas tabaci* IFO3508. *Pseudomonas taetrolens* IFO3460, *Pseudomonas vesicularis* JCM1477t, *Rhodobacter sphaeroides* ATCC17023, *Rhodococcus erythropolis* IFO12320, *Rhodococcus groberulus* ATCC15610, *Rhodococcus rhodochrous* JCM3202t, *Rhodococcus rhodochrous* ATCC15610, *Rhodococcus* sp. ATCC19148, and the like.

The microorganism is preferably at least one kind of microorganism selected from the group consisting of genus *Alcaligenes*, genus *Bacillus*, genus *Pseudomonas*, genus *Rhodobacter* and genus *Rhodococcus*. The microorganism is more preferably at least one kind of microorganism selected from the group consisting of genus *Bacillus*, genus *Pseudomonas* and genus *Rhodococcus*, even more preferably at least one kind of microorganism selected from the group consisting of genus *Pseudomonas* and genus *Rhodococcus*, and specifically preferably a microorganism of genus *Rhodococcus*.

Using a cell or a material from treated cell of such a microorganism as a catalyst, the primary hydroxyl group of the sulfur-containing dihydroxy compound represented by the general formula (1) can be preferentially oxidized. As used herein, the term "can be preferentially oxidized" means that the oxidization of the primary hydroxyl group of the sulfur-containing dihydroxy compound proceeds in preference to the oxidation of the secondary hydroxyl group and sulfide of the sulfur-containing dihydroxy compound.

Secondly, the method for preparing the microorganism used for the present invention is explained.

The microorganism can be cultured using various media for culturing microorganisms that suitably comprise a carbon source, a nitrogen source, organic salts, inorganic salts, and the like.

Examples of the carbon source included in the medium may include glucose, sucrose, glycerol, starch, organic acids, molasses, and the like. Examples of the nitrogen source may include yeast extracts, meat extracts, peptone, casamino acid, malt extracts, soybean powder, corn steep liquor, cottonseed powder, dry yeast, ammonium sulfide, sodium nitrate, and the like. Examples of the organic acid salt and inorganic acid salt may include sodium chloride, potassium chloride, sodium carbonate, potassium phosphate, dipotassium phosphate, calcium carbonate, ammonium acetate, magnesium sulfate, copper sulfate, zinc sulfate, ferrous sulfate, cobalt chloride, and the like.

Examples of methods for culturing may include solid culturing, liquid culturing (test tube culturing, flask culturing, jar fermenter culturing, and the like), and the like.

The temperature for culturing and the pH of the culture are not specifically limited within the range where the present microorganism grows. For example, the culture temperature may be in the range of from about 15° C. to about 45° C., and the pH of the culture may be in the range of from about 4 to about 8. The culture time can be suitably selected according to the condition for culturing, and generally in the range from about 1 day to 7 days.

The cell of the microorganism can be directly used as a catalyst for the process of the present invention. Examples of the method comprising directly using a cell of a microorganism may include (1) a method comprising directly using a culture, (2) a method comprising collecting cells by such as centrifugation of a culture and using the collected cells (where necessary, wet cells washed with buffer or water), and the like.

Alternatively, a material from treated cell of the microorganism may be used as a catalyst used for the present invention. Examples of the material from treated cell may include cells obtained by culturing, followed by treating with an organic solvent (acetone, ethanol, and the like), lyophilizing or treating with an alkaline; or physically or enzymatically disrupted cells, or crude enzymes obtained by separation or extraction from those cells, or purified enzymes obtained by purifying the crude enzymes, or the like. Furthermore, examples of the material from treated cell may also include cells subjected to the above-mentioned treatment and fixed by a publicly known method.

The present invention is generally carried out in the presence of water. In this case, water may be in the form of a buffer. Examples of buffer agents used for the buffer include alkali metal salts of phosphoric acid such as sodium phosphate and potassium phosphate, alkali metal salts of acetic acid such as sodium acetate and potassium acetate, and the like.

Alternatively, the present invention can be carried out in the presence of water and a hydrophobic organic solvent by additionally using a hydrophobic organic solvent. Examples of the hydrophobic organic solvent used in this case may include esters such as ethyl formate, ethyl acetate, propyl acetate, butyl acetate, ethyl propionate, and butyl propionate, alcohols such as n-butylalcohol, n-amylalcohol, and n-octylalcohol, aromatic hydrocarbons such as benzene, toluene, and xylene, ethers such as diethyl ether, diisopropyl ether, and methyl t-butyl ether, halogenated hydrocarbons such as chloroform and 1,2-dichloroethane, and mixtures thereof.

Alternatively, the present invention can be carried out in the presence of water and an aqueous medium, by additionally using a hydrophilic organic solvent. Examples of the hydrophilic organic solvent used in this case may include alcohols such as methanol and ethanol, ketones such as acetone, ethers such as dimethoxyethane, tetrahydrofuran, and dioxane, and mixtures thereof.

Although the reaction pH in the present invention is generally pH 3 to 10 for the aqueous layer, it can be suitably varied in the range in which the reaction proceeds.

Although the reaction temperature in the present invention is generally from about 0° C. to 60° C., it can be suitably varied in the range in which the reaction proceeds.

The reaction time for the present invention is generally in the range from about 0.5 hour to about 10 days. The end point of the reaction can be checked by measuring the amount of the sulfur-containing dihydroxy compound in the reaction solution after completion of addition of the sulfur-containing dihydroxy compound, which is a raw material compound, by liquid chromatography, gas chromatography, and the like.

The concentration of the sulfur-containing dihydroxy compound, which is a raw material compound for the present invention, is generally 50% (w/v) or less. In order to keep the concentration of the sulfur-containing dihydroxy compound approximately constant in the reaction system, the sulfur-containing dihydroxy, compound may be added to the reaction system continuously or successively.

In the present invention, if necessary, a sugar such as glucose, sucrose, and fructose, or a surfactant such as Triton X-100 and Tween 60 may be added to the reaction system.

After the reaction is completed, the reaction solution is subjected to a general post-treatment such as organic solvent extraction and concentration, whereby the sulfur-containing hydroxycarboxylic acid compound corresponding to the sulfur-containing dihydroxy compound can be collected from the reaction solution. The thus-collected sulfur-containing hydroxycarboxylic acid compound may be further purified by column chromatography, evaporation, and the like, if necessary.

EXAMPLES

Hereinafter the present invention is explained in more detail based on Examples. However, it is needless to say that the present invention is not limited by the Examples.

Production Example 1

Production of a Raw Material, 4-(methylthio)butane-1,2-diol

A 100 mL flask with a magnetic stirrer was charged with 3-butene-1,2-diol (880 mg) and azobisisobutyronitrile (10 mg). The mixture was bubbled with methanethiol for 1 hour under stirring while keeping the temperature at 25° C. The mixture was stirred for additional 1 hour at the same temperature and then bubbled with nitrogen for 0.5 hour to purge the residual methanethiol, whereby colorless oil (1245 mg) was finally obtained. The oil was analyzed by gas chromatography area percentage method, which revealed the yield of 4-(methylthio)butane-1,2-diol to be 72.5%. The amount of the unreacted residual 3-butene-1,2-diol was 26.6% of the amount that was initially charged.

Water was then added to the thus-obtained colorless oil so that the concentration of 4-(methylthio)butane-1,2-diol became 10% (w/v). The insoluble fraction (i.e., azobisisobutyronitrile) was removed from the mixture by filtration to afford a raw material (10% (w/v) aqueous solution of 4-(methylthio)butane-1,2-diol), which was used for Example 1.

Example 1

Production Example of a Sulfur-Containing Hydroxycarboxylic Acid Compound from a Sulfur-Containing Dihydroxy Compound According to the Process of the Present Invention Test tubes were charged with a sterilized medium (5 ml), which was prepared by adding glucose (20 g), polypeptone (5 g), yeast extract (3 g), meat extract (3 g), ammonium sulfate (0.2 g), potassium dihydrogenphosphate (1 g) and magnesium sulfate 7-hydrate (0.5 g) to water (1 L) and adjusting the pH to 7.0. The cells shown in Table 1 were inoculated into the medium. Each medium was subjected to shaking culturing at 30° C. under aerobic condition. After the culturing was completed, the cells were separated by centrifugation to afford viable cells. A test tube with a screw cap was charged with 0.1 M Potassium phosphate buffer (pH 7) (2 ml), and the above-mentioned viable cells were added thereto and suspended. The raw material (0.2 ml) obtained by Production Example 1 (10% (w/v) aqueous solution of 4-(methylthio)butane-1,2-diol) was added to the suspension so that the final concentration of 4-(methylthio)butane-1,2-diol became 10% (w/v), and the obtained mixture was shaken at 30° C. for 2 or 3 days.

After the reaction was completed, the reaction solution (1 ml) was sampled. The cells were removed from the sampling solution, and the amount of produced 2-hydroxy-4-methylthiobutyric acid was analyzed by liquid chromatography. The obtained results are shown in Tables 1 to 4.

(Condition of content analysis)
Column: Cadenza CD-C18 (4.6 mmϕ × 15 cm, 3 μm) (manufactured by Imtakt Corporation)
Mobile phase: liquid A: 0.1% trifluoroacetic acid aqueous solution, liquid B: methanol

| Time (min) | liquid A (%):liquid B (%) |
|---|---|
| 0 | 80:20 |
| 10 | 80:20 |
| 20 | 50:50 |
| 30 | 50:50 |
| 30.1 | 80:20 |

Flow: 0.5 ml/min
Column temperature: 40° C.
Detection: 220 nm

TABLE 1

| Name of strain | Production rate of 2-hydroxy-4-methylthio-butyric acid (%) |
|---|---|
| Alcaligenes faecalis IFO 13111t | 0.1 |
| Alcaligenes denitrificans JCM 5490 | 0.4 |
| Alcaligenes eutrophus ATCC 43123 | 0.1 |
| Alcaligenes faecalis IFO 12669 | 0.2 |
| Alcaligenes faecalis IFO 14479 | 0.1 |
| Alcaligenes faecalis JCM 5485t | 2.5 |
| Alcaligenes sp. IFO 14130 | 0.1 |
| Alcaligenes xylosoxydans IFO15125t denitrificans | 0.2 |
| Alcaligenes xylosoxydans IFO15126t xylosoxydans | 0.5 |
| Bacillus alvei IFO 3343t | 17.0 |
| Bacillus badius ATCC 14574t | 7.3 |
| Bacillus brevis IFO 12334 | 4.7 |
| Bacillus brevis JCM 2503t | 4.2 |
| Bacillus cereus JCM 2152t | 11.2 |
| Bacillus cereus var. juroi ATCC 21281 | 10.3 |
| Bacillus cereus var. mycoides IFO 3039 | 2.6 |
| Bacillus circulans ATCC 13403 | 1.2 |
| Bacillus circulans IFO 3329 | 2.8 |
| Bacillus circulans JCM 2504t | 1.4 |
| Bacillus coagulans JCM 2257t | 5.0 |
| Bacillus firmus JCM 2512t | 0.6 |
| Bacillus lentus JCM 2511t | 3.6 |
| Bacillus licheniformis ATCC 27811 | 2.0 |
| Bacillus licheniformis IFO 12195 | 1.8 |
| Bacillus licheniformis IFO 12195 | 1.3 |
| Bacillus licheniformis IFO 12197 | 12.9 |
| Bacillus licheniformis IFO 12200t | 1.3 |
| Bacillus macerans JCM 2500t | 1.5 |
| Bacillus megaterium IFO 12108 | 0.6 |
| Bacillus megaterium JCM 2506t | 1.2 |

TABLE 2

| Name of strain | Production rate of 2-hydroxy-4-methylthio-butyric acid (%) |
|---|---|
| Bacillus moritai ATCC 21282 | 11.5 |
| Bacillus mycoides IFO 3039 | 6.0 |
| Bacillus polymyxa IFO 3020 | 3.5 |
| Bacillus polymyxa JCM 2507t | 2.8 |
| Bacillus pumilus IFO 12092t | 1.5 |
| Bacillus sphaericus IFO 3341 | 13.2 |
| Bacillus sphaericus IFO 3525 | 0.6 |
| Bacillus sphaericus IFO 3526 | 6.2 |
| Bacillus sphaericus IFO 3527 | 4.0 |
| Bacillus sphaericus IFO 3528 | 1.6 |
| Bacillus subtilis JCM 1465t | 10.8 |
| Bacillus subtilis ATCC 14593 | 1.7 |
| Bacillus subtilis ATCC 15841 | 5.6 |
| Bacillus subtilis IFO 03026 | 2.8 |
| Bacillus subtilis IFO 03108 | 2.5 |
| Bacillus subtilis IFO 03134 | 2.8 |
| Bacillus subtilis IFO 3026 | 3.3 |
| Bacillus subtilis IFO 3037 | 2.7 |
| Bacillus subtilis IFO 3108 | 1.7 |
| Bacillus subtilis IFO 3134 | 1.5 |
| Bacillus thuringensis ATCC 13366 | 10.4 |
| Bacillus validus IFO 13635 | 3.8 |
| Pseudomonas auricularis IFO 13334t | 1.9 |
| Pseudomonas azotoformans JCM 2777t | 8.9 |
| Pseudomonas caryophylli IFO 13591 | 0.4 |
| Pseudomonas chlororaphis IFO 3521t | 1.1 |
| Pseudomonas chlororaphis IFO 3904t | 0.7 |
| Pseudomonas denitrificans IAM 1923 | 2.7 |
| Pseudomonas diminuta JCM 2788t | 38.9 |

TABLE 3

| Name of strain | Production rate of 2-hydroxy-4-methylthio-butyric acid (%) |
|---|---|
| Pseudomonas fluorescens Biotype F ATCC 17513 | 7.6 |
| Pseudomonas fluorescens IFO 14160t | 0.3 |
| Pseudomonas fragi IAM12402 | 0.1 |
| Pseudomonas fragi IFO 3458t | 0.4 |
| Pseudomonas fulva JCM 2780t | 1.1 |
| Pseudomonas mendocina IFO 14162 | 34.1 |
| Pseudomonas mutabilis ATCC31014 | 13.5 |
| Pseudomonas nitroreducens JCM 2782t | 8.4 |
| Pseudomonas oleovorans IFO 13583t | 0.3 |
| Pseudomonas ovalis IFO 12688 | 1.4 |
| Pseudomonas oxalaticus IFO 13593t | 0.2 |
| Pseudomonas plantarii JCM 5492t | 1.3 |
| Pseudomonas pseudoalcaligenes JCM 5968t | 36.2 |
| Pseudomonas putida ATCC 17428 | 1.5 |
| Pseudomonas putida ATCC 17484 | 9.9 |
| Pseudomonas putida ATCC39213 | 23.3 |
| Pseudomonas putida IAM 1002 | 20.5 |
| Pseudomonas putida IAM 1090 | 28.1 |
| Pseudomonas putida IAM 1094 | 1.0 |
| Pseudomonas putida IAM 1236 | 19.6 |
| Pseudomonas putida IFO 12996 | 5.6 |
| Pseudomonas putida IFO 13696 | 9.3 |
| Pseudomonas putida IFO 14164t | 41.2 |
| Pseudomonas putida IFO 14671 | 0.9 |
| Pseudomonas putida IFO 14796 | 1.0 |
| Pseudomonas putida IFO 3738 | 38.2 |
| Pseudomonas putida IFO12653 | 5.7 |
| Pseudomonas putida JCM 6156 | 1.5 |
| Pseudomonas putida JCM 6157 | 0.5 |
| Pseudomonas putida JCM 6158 | 1.2 |

TABLE 4

| Name of strain | Production rate of 2-hydroxy-4-methylthio-butyric acid (%) |
| --- | --- |
| *Pseudomonas putrefaciens* IFO 3910 | 0.2 |
| *Pseudomonas riboflavina* IFO 13584t | 0.1 |
| *Pseudomonas* sp. ATCC 53617 | 4.4 |
| *Pseudomonas straminea* JCM 2783t | 1.0 |
| *Pseudomonas synxantha* IFO 3913t | 0.4 |
| *Pseudomonas syringae* subsp. *syringae* IFO14055 | 3.8 |
| *Pseudomonas tabaci* IFO 3508 | 1.7 |
| *Pseudomonas taetrolens* IFO 3460 | 0.3 |
| *Pseudomonas vesicularis* JCM 1477t | 8.4 |
| *Rhodobacter sphaeroides* ATCC 17023 | 3.0 |
| *Rhodococcus erythropolis* IFO 12320 | 21.7 |
| *Rhodococcus globerulus* ATCC 15076 | 22.7 |
| *Rhodococcus rhodochrous* ATCC 15610 | 58.9 |
| *Rhodococcus rhodochrous* ATCC 19067 | 16.0 |
| *Rhodococcus rhodochrous* ATCC 19149 | 14.6 |
| *Rhodococcus rhodochrous* ATCC 19150 | 12.3 |
| *Rhodococcus rhodochrous* ATCC 21197 | 2.7 |
| *Rhodococcus rhodochrous* ATCC 21199 | 7.9 |
| *Rhodococcus rhodochrous* JCM 3202t | 30.9 |
| *Rhodococcus* sp ATCC 19070 | 13.1 |
| *Rhodococcus* sp ATCC 19071 | 7.7 |
| *Rhodococcus* sp ATCC 19148 | 34.5 |

INDUSTRIAL APPLICABILITY

According to the present invention, it becomes possible to produce a sulfur-containing hydroxycarboxylic acid compound efficiently.

The invention claimed is:

1. A process for producing a sulfur-containing α-hydroxycarboxylic acid compound represented by the formula (2):

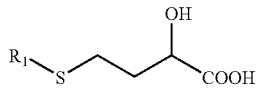

(2)

wherein $R_1$ represents a hydrogen atom, an alkyl group having 1 to 8 carbon atoms or an aryl group having 6 to 20 carbon atoms, which comprises a step for reacting a sulfur-containing dihydroxy compound represented by the formula (1):

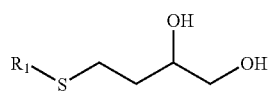

(1)

wherein $R_1$ is as defined above, with a cell or a material from a treated cell of a microorganism that has an ability to convert the sulfur-containing dihydroxy compound to a corresponding α-hydroxycarboxylic acid compound, wherein the microorganism is at least one kind of microorganism selected from the group consisting of genus *Alcaligenes*, genus *Bacillus*, genus *Pseudomonas*, genus *Rhodobacter* and genus *Rhodococcus*.

2. The process according to claim 1, wherein $R_1$ in the sulfur-containing dihydroxy compound represented by the formula (1) is an alkyl group having 1 to 8 carbon atoms.

\* \* \* \* \*